United States Patent [19]

Meilland

[11] Patent Number: Plant 6,384

[45] Date of Patent: Nov. 8, 1988

[54] ROSE PLANT — MEIGEKANU VARIETY

[75] Inventor: Marie-Louise Meilland, Antibes, France

[73] Assignee: The Conard-Pyle Company, West Grove, Pa.

[21] Appl. No.: 895,451

[22] Filed: Aug. 11, 1986

[51] Int. Cl.[4] ..... A01H 5/00

[52] U.S. Cl. ..... Plt./1

[58] Field of Search ..... Plt./1, 28–29

*Primary Examiner*—Robert E. Bagwill

*Attorney, Agent, or Firm*—Burns, Doane, Swecker & Mathis

[57] ABSTRACT

A new and distinct variety of shrub rose plant is provided which forms attractive semi-double brilliant luminous red blossoms. The new variety has a well-branched semi-erect growth habit and is well adapted for growing in the landscape where it reflowers well all season long. Asexual propagation readily can be carried out through the use of cuttings. Above average disease resistance also is exhibited.

1 Drawing Sheet

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) of the new variety was formed by a pair of crosses. More specifically, the product of a cross between the Meibrem 172F variety and the Meialfi 218F was crossed with the Tropicana variety (U.S. Plant Pat. No. 1,969) to form the female parent. The male parent (i.e., the pollen parent) of the new variety was the Meilena 0735F variety. The parentage of the new variety can be summarized as follows:

[(MEIBREM 172F×MEIALFI 218F)×TROPICANA]×MEILENA 0735F.

The seeds resulting from the above pollination were sown and 705 plantlets were obtained which were physically and biologically different from each other. Selective study resulted in the identification of a single plant of the new variety.

It was found that the new variety of shrub rose plant of the present invention possesses the following combination of characteristics:

(a) forms throughout the season attractive semi-double bright red blossoms,
(b) exhibits a well-branched semi-erect growth habit,
(c) exhibits above-average disease resistance,
(d) exhibits a propensity to readily undergo asexual propagation from cuttings, and
(e) is particularly well-suited for growing in the landscape.

The new variety meets the needs of the horticultural industry for all uses. It can be grown to advantage as an attractive ornamentation in parks, gardens, public areas, and residential landscapes.

The characteristics of the new variety have been found to be homogeneous and stable and are strictly transmissible by asexual propagation from one generation to another.

The new variety has been named the Meigekanu variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were grown outdoors at Cannet des Maures, Var, France.

DETAILED DESCRIPTION

Figures 1, 2, 3, 4, 5, 6, 7, 8, 9, 10, 11, 12, 13, 14, 15:
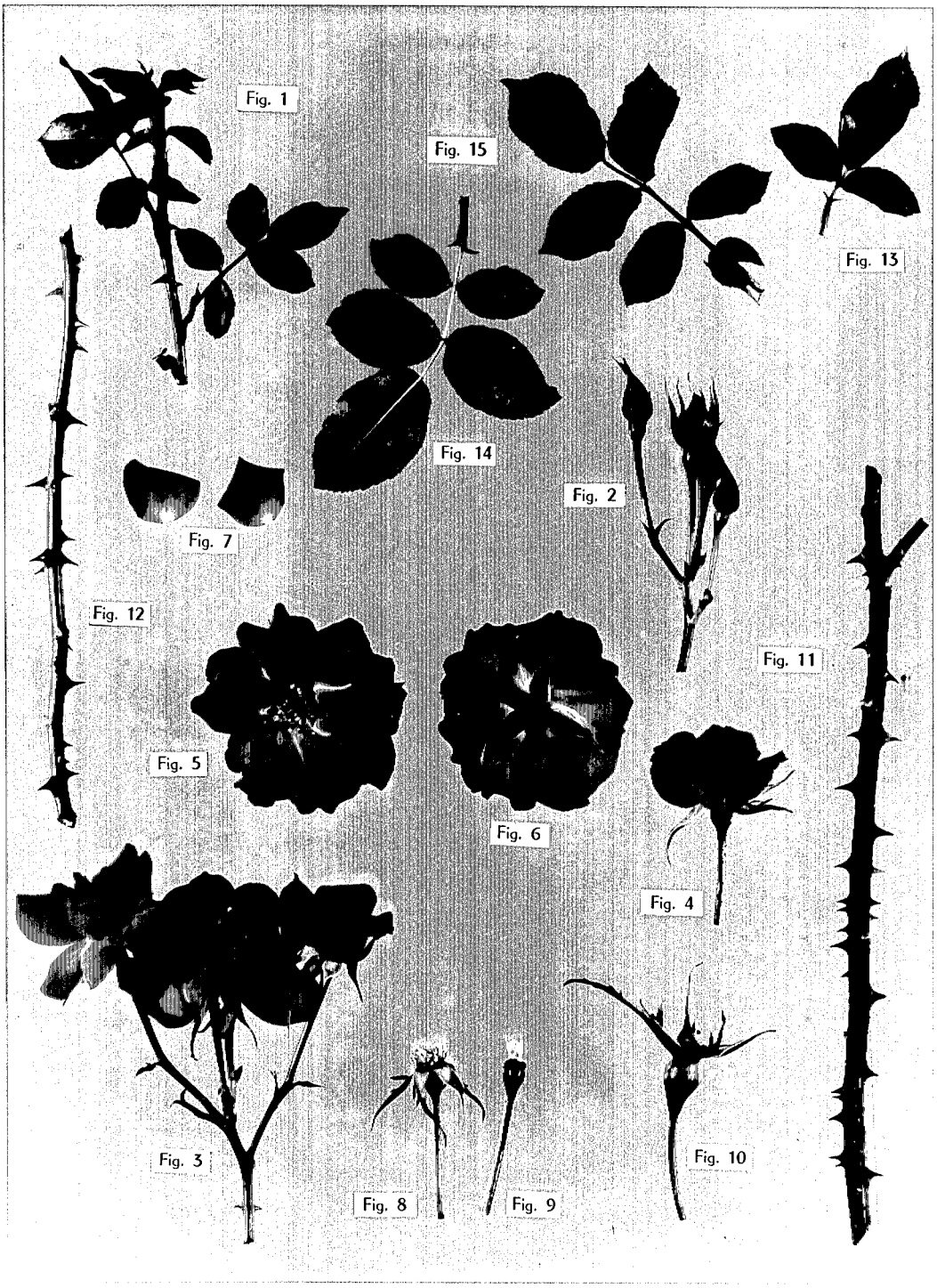
FIG. 1 illustrates a specimen of a young shoot.
FIG. 2 illustrates a specimen of four flowering buds showing three buds before the opening of the sepals and one bud as the sepals open.
FIG. 3 illustrates a specimen of a cluster of flowers showing a bud at the opening of the sepals and buds and blossoms in various stages of opening.
FIG. 4 illustrates a specimen of a flower in the course of opening.
FIG. 5 illustrates a specimen of an open flower — plan view — obverse.
FIG. 6 illustrates a specimen of an open flower — plan view — reverse.
FIG. 7 illustrates specimens of petals with the one on the left showing the under surface and the one on the right showing the upper surface.
FIG. 8 illustrates a specimen of a floral receptacle showing the arrangement of the stamens and pistils.
FIG. 9 illustrates a specimen of a floral receptacle showing the arrangement of the pistils (stamens removed)
FIG. 10 illustrates a specimen of a fruit.
FIG. 11 illustrates a specimen of a main branch.
FIG. 12 illustrates a specimen of a flowering stem.
FIG. 13 illustrates a specimen of a leaf with three leaflets — upper surface.
FIG. 14 illustrates a leaf with five leaflets — under surface.
FIG. 15 illustrates a specimen of a leaf with seven leaflets — upper surface.

The chart used in the identification of the colors is that of The Royal Horticultural Society (R.H.S. Colour Chart). The terminology preceding the numbered references has been added to designate in common terms the corresponding colors. The description is based on specimens of the new variety while grown outdoors at Cannet des Maures, Var, France.

Class: Shrub.

Plant:

*Height.*—Approximately 80 to 85 cm. on average.

*Habit.*—Bushy, semi-erect.

Branches:

*Color.*—Young stems: light green, Yellow-Green Group 144A, somewhat shaded with reddish brown. Adult wood: Yellow-Green Group 146B.

Leaves:

*Petioles.*—Upper surface: grooved, reddish on young foliage, medium green on adult foliage. Under surface: light green.

*Leaflets.*—Number: 3, 5, and 7 (most often). Shape: oval, rounded at the base and pointed at the apex. Serration: simple and regular. Texture: leathery. Color (young foliage): upper surface: dark green, Yellow-Green Group 147A, with strong bronze shading; under surface: light green, Yellow-Green Group 147C. Color (adult foliage): upper surface: slightly lighter than Green Group 136A; under surface: light green, Yellow-Green Group 146D.

Inflorescence:

*Number of flowers.*—Commonly approximately 5 to 20 per stem.

*Peduncle.*—Straight, rigid, glandular, more or less spotted with reddish-brown coloration.

*Buds.*—Shape: conical. Length: approximately 2.1 cm. on average at the opening of the sepals and not including the calyx. Color: upper surface: bright red, slightly lighter than Red Group 45B, extremely luminous; under surface: Turkish red, Red Group 46C, dull.

*Flower.*—Form: semi-double, opens somewhat rapidly, petals are prominent, stamens are apparent, blossoms tend to be flat in configuration immediately prior to petal drop. Diameter: Approximately 8 cm. on average. Color (when opening begins): upper surface: Red Group 45B, extremely luminous; under surface: Red Group 46C, dull. Color (when partially open): upper surface: bright red, slightly lighter than Red Group 45B, very luminous; under surface: Red Group 46C, dull. Color (at end of opening): upper surface: bright red, Red Group 45C, a little less bright than in the process of opening, shaded with Red Group 45D at the base of the petals, and lightly crimsoned at the petal borders; under surface: Red Group 46C, dull. Fragrance: none. Lasting quality: average. Petal form: the upper surface is substantially rounded with a small point at the apex, some of the center petals commonly exhibit a longitudinal white stripe, and a white area commonly is present on both sides of the petals at the base. Petal number: approximately 10 to 15 on average including some at the center which are not always entire. Stamen number: approximately 117 on average. Anthers: normal and yellow in coloration. Pistils: approximately 45 on average.

Development:

*Vegetation.*—Well-branched.

*Blossoming.*—Continuous throughout season.

*Disease resistance.*—Above average.

I claim:

1. A new and distinct variety of shrub rose plant characterized by the following combination of characteristics:

(a) forms throughout the season attractive semi-double bright red blossoms, (b) exhibits a well-branched semi-erect growth habit, (c) exhibits above-average disease resistance, (d) exhibits a propensity to readily undergo asexual propagation from cuttings, and (e) is particularly well-suited for growing in the landscape;

substantially as herein shown and described together with the parts thereof.

* * * * *